United States Patent [19]

France et al.

[11] Patent Number: 5,538,486
[45] Date of Patent: Jul. 23, 1996

[54] INSTRUMENTED THERAPY CORD

[75] Inventors: E. Paul France; Earl Van Wagoner, both of Salt Lake City, Utah

[73] Assignee: Hoggan Health Industries, Inc., Draper, Utah

[21] Appl. No.: 253,970

[22] Filed: Jun. 3, 1994

[51] Int. Cl.$^6$ .................................................. A63B 69/00
[52] U.S. Cl. ........................ 482/8; 482/1; 482/5; 482/4; 482/121
[58] Field of Search .............................. 482/1–8, 49, 54, 482/73, 121, 906; 73/379.08

[56] References Cited

U.S. PATENT DOCUMENTS

| | | |
|---|---|---|
| 3,498,609 | 3/1970 | Lukens . |
| 3,989,240 | 11/1976 | Victor et al. . |
| 4,231,255 | 11/1980 | Haski et al. . |
| 4,307,608 | 12/1981 | Useldinger et al. . |
| 4,501,148 | 2/1985 | Nicholas et al. . |
| 4,572,511 | 2/1986 | Barringer ........................ 482/906 X |
| 4,607,841 | 8/1986 | Gala . |
| 4,613,130 | 9/1986 | Watson . |
| 4,824,103 | 4/1989 | Smidt . |
| 4,875,674 | 10/1989 | Dreissigacker et al. . |
| 4,884,800 | 12/1989 | Duke .................................... 482/73 |
| 4,907,795 | 3/1990 | Shaw et al. . |
| 4,912,638 | 3/1990 | Pratt, Jr. . |
| 5,052,375 | 10/1991 | Stark et al. . |
| 5,205,803 | 4/1993 | Zemitis . |
| 5,222,926 | 6/1993 | Eggen . |
| 5,318,491 | 6/1994 | Houston ............................. 482/54 |
| 5,362,295 | 11/1994 | Nurge ................................ 482/49 X |

Primary Examiner—Richard J. Apley
Assistant Examiner—Glenn E. Richman
Attorney, Agent, or Firm—Berne S. Broadbent; Gary D. E. Pierce; A. John Pate

[57] ABSTRACT

An instrumented therapy cord including a load cell transducer, a resistive stretch cord and a microprocessor control module having internal memory capacity and programming means for assessing, monitoring and controlling rehabilitation treatment programs. Operably attached to a handle member and preferably incorporated within a housing unit, the microprocessor control module interfaces with the load cell transducer. A first end of the resistive therapy stretch cord is operably coupled to the load cell transducer by a permanent or quick-release coupling means. A second end of the resistive therapy cord is removably connected to a second handle or stationary body. The operable connection between the resistive therapy cord and the load cell transducer interfacing with the microprocessor provides means for processing and displaying direct measure and description of force peak and average loads, number of load repetitions, load profiles and frequencies of cord tension applied to the resistive therapy stretch cord by a user. The microprocessor control module includes means for providing auditory and visual feedback for use in a biofeedback mode to control and monitor force applications applied to the body system being conditioned. The internal memory of the microprocessor control module processes and stores biofeedback generated by the load cell transducer for analysis and utilization in therapy evaluation and planning to eliminate mere subjective evaluation of patient rehabilitation performance.

28 Claims, 3 Drawing Sheets

INSTRUMENTED THERAPY CORD

BACKGROUND

1. The Field of the Invention

This invention relates to physical therapy devices and, more particularly, to novel systems and methods for instrumenting a resistive therapy cord.

2. The Background Art

Physical therapy is a key element in the treatment of musculoskeletal disabilities. Current therapy practices generally include rehabilitative techniques to strengthen muscles, encourage proprioception and retrain neural pathways. The advantages of therapeutic exercise typically involve the development, improvement, restoration or maintenance of a patient's normal level of strength, endurance, coordination, mobility and flexibility.

In therapeutic exercises, stresses and forces are applied to body systems in a positive, progressive and appropriately planned manner to ultimately improve the overall function of an affected body system. Traditionally, the overwhelming objective of a rehabilitation therapy program is to return the individual to as normal and full a lifestyle as possible, or, alternatively, to maintain or to maximize remaining function of the body systems.

In order to effectively administer therapeutic exercise to a patient, a physician, therapist, and/or other health care provider must generally understand the basic principles and effects of various therapy treatments, be able to facilitate a functional evaluation of the patient and possess a working knowledge of the interrelationships of the anatomy and kinesiology of the body systems. In addition, the physician or therapist should generally be aware of the state of the patient's disability and the potential rate of recovery, complications, precautions and contraindications.

Typically, the first step in conducting a therapeutic treatment protocol is to assess the patient's injury using an evaluation process to gather subjective information and objective data about the patient and his/her physical condition. Systematic tests are generally administered to assist in defining the anatomic structure or structures involved and the functional limitations experienced by the patient. These evaluation procedures may include, for example, posture evaluations, goniometric measurements, manual muscle testing and/or other systematic orthopedic evaluation procedures. Once a patient's complications and/or disease are assessed and diagnosed, a treatment plan is typically established.

It is well known that the human body and the individual body systems react and develop in response to the forces and stresses placed upon them. Accordingly, the absence of normal stresses on body systems can lead to injury and possible deformity. For example, the absence of normal weight bearing forces, associated with prolonged bed rest, or the absence of normal muscle pull on bone, as seen in flaccid paralysis, may cause muscle atrophy and osteoporosis. Similarly, prolonged inactivity may lead to decreased efficiency of the respiratory and circulatory systems.

If the normal motion of a body system is restricted in any way, adaptive shortening or tightening of soft tissues and joints generally occurs which may cause long-term static and often faulty positioning of the affected joints and soft tissue. In this regard, a significant goal of therapeutic exercise is the development, enhancement and/or maintenance of muscle strength and endurance.

Strength is the ability of a muscle or muscle group to produce tension and a resulting force in one maximal effort, either dynamically or statically, in relation to the demands placed upon it. As a muscle contracts and develops tension, a responsive force is typically exerted by the muscle. The amount of force produced depends on a wide variety of biomechanical, physiological and neuromuscular factors.

Endurance is essential for performing repeated motor tasks in daily living and to carry on a sustained level of functional activity, such as walking or climbing stairs. As generally defined, muscle endurance is the ability of a muscle to contract repeatedly or generate tension and sustain that tension over a prolonged period of time. As endurance increases, a muscle or muscle group is typically able to perform a greater number of contractions and hold against a load force over an extended period of time. Accordingly, active exercise performed repeatedly against a moderate load to the point of fatigue generally increases the strength and endurance of a muscle or muscle group.

If resistance is applied to a muscle as it contracts, the muscle will generally become stronger over a period of time. Adaptive changes typically occur in a muscle or muscle group through the use of rehabilitative therapeutic exercise as long as the metabolic capabilities of the muscle are progressively overloaded. As the strength of a muscle increases, the cardiovascular response of the muscle typically improves so that muscular endurance also increases.

The rehabilitative and therapeutic use of resistance in an exercise program, whether applied manually or through mechanical instrumentation, is an integral part of a patient's plan of care when the ultimate goal is to improve strength, endurance and overall physical function of an affected body system. Resistance exercise is traditionally categorized as any form of active exercise in which a dynamic or static muscular contraction is resisted by an outside force. For example, active manual resistance is a form of isometric exercise in which the resistance applied to a muscle or muscle group is generally provided directly by the physician, therapist or other health care provider. Isometric exercise, by general definition, is a "static" form of exercise that occurs when a muscle contracts without any appreciable change in the length of the muscle or without visible joint motion. Although the amount of resistance applied is not typically measured quantitatively, manual resistance is generally useful in the early stages of a therapeutic exercise program when the muscle to be strengthened is weak and can overcome only mild to moderate resistance.

A significant disadvantage with manual resistance exercise, however, is that the amount of static resistance applied against a patient's body system is generally limited by the strength of the attending physician or therapist. Although several attempts to standardize manual isometric testing procedures have been proposed and various devices to measure strength have been developed by those skilled in the art, manual muscle testing, without instrumentation, continues to be the predominant method used in clinical settings despite the obvious disadvantages associated with subjective testing of muscle strength.

Other techniques of resistance exercise typically utilize mechanical instrumentation to provide "dynamic" resistance in which the resistance is applied through the use of equipment or mechanical apparatus. For example, isotonic resistance is carried out against the resistance provided as a muscle lengthens or shortens through its range of motion. When a load is lifted or lowered, a muscle or muscle group typically contracts either concentrically or eccentrically. In addition, isokinetic exercise is another form of dynamic resistance in which the velocity of muscle shortening is typically controlled by a mechanical rate-limiting device which regulates and limits the speed of movement of the body system.

Passive-resistive therapy stretch cords were developed by those skilled in the art as a "dynamic" mechanical means to assist in providing strengthening exercises and rehabilitation for the upper and lower extremities and the back. Typically, prior art therapy stretch cords are versatile, flexible, relatively inexpensive and easily stored. However, because the amount of resistance force which can be provided by therapy stretch cords of the prior art is not presently measurable, the utility of resistive stretch cords is limited in its therapeutic application. Without means for providing biofeedback, it is generally difficult for a physician or therapist to determine the proper stretch cord resistance force to apply to a patient for a safe, yet effective therapeutic treatment. Moreover, measuring a patient's muscle or joint compliance without means for monitoring the patient biofeedback, typically restricts the general rehabilitative utility and application of prior art resistive therapy cords.

Because physicians and therapists traditionally rely on subjective determinations to measure a patient's progress, prior art resistive stretch cords are currently being used by those skilled in the art as a therapy and conditioning tool without the benefit or capacity to measure muscle force peaks, averages, profiles and/or frequencies applied to the resistive stretch cord. Whereby, it would be medically desirable as a rehabilitative or strengthening means to provide an instrumented therapy stretch cord which measures and displays the amount of force exerted by a user during therapeutic exercise, thereby providing objective biofeedback which is subsequently invaluable to a patient's treatment evaluation and therapeutic program.

Although the prior art discloses microprocessor-controlled therapy devices which are purportedly designed for use in measuring, monitoring and recording forces and/or repetitions during exercise, efforts to quantify a patient's rehabilitation performance during isotonic or isokinetic resistive exercise are generally underdeveloped despite the instrumentation capabilities and pressures from the health care system to objectively evaluate treatment efficacy. In this regard, the National Institute of Health (NIH) task force on medical rehabilitation recently explained that a foremost priority is the thorough evaluation of existing and newly developed therapeutic and rehabilitation devices for providing accurate outcome measurements. In particular, the meaningfulness, reliability and validity of these measurements must be ascertainable by the physician and/or therapist for evaluation purposes. In accordance therewith, it would be desirable as a therapeutic and rehabilitative means to provide an instrumented therapy cord which measures and displays as biofeedback the amount of force exerted by the user during therapeutic resistive exercise.

BRIEF SUMMARY AND OBJECTS OF THE INVENTION

In view of the foregoing, it is a primary object of the present invention to provide an instrumented therapy cord having a microprocessor control module and load cell transducer which are capable of providing means for displaying direct measure and description of force peaks, average loads, number of load repetitions, profiles and frequencies applied to a resistive therapy stretch cord by a user.

It is also an object of the present invention to provide an instrumented therapy cord which is capable of providing auditory and visual biofeedback to a patient, physician and/or therapist to provide means for assessing, monitoring and controlling the patient's therapeutic treatment program.

It is a further object of the present invention to provide an instrumented therapy cord which is capable of providing meaningful, reliable and valid measure of therapeutic exercise for outcome evaluation or assessment, thereby eliminating the need for mere subjective evaluation of a patient's rehabilitative performance.

It is a still further object of the present invention to provide an instrumented therapy cord which incorporates a microprocessor control module having internal memory capacity or external memory interface capacity for storing and retrieving patient biofeedback data generated by the load cell transducer for review, evaluation and/or manipulation by a physician and/or therapist.

Consistent with the foregoing objects, and in accordance with the invention as embodied and broadly described herein, an instrumented therapy cord is disclosed in one preferred embodiment of the present invention as comprising a handle member, a resistive stretch cord, a load cell transducer and a microprocessor control module having internal memory capacity and programming means for assessing, monitoring and controlling rehabilitation treatment programs. Operably attached to the handle member and preferably incorporated within a housing unit, the microprocessor control module electronically interfaces with the load cell transducer. A first end of the resistive stretch cord is connected to the load cell transducer by means of a permanent or quick-release coupling. A second end of the resistive therapy cord is preferably removably connected to a stationary body or second handle member. The operable connection between the resistive therapy cord and the load cell transducer interfacing with the microprocessor control module provides means for displaying direct measure and description of force peak and average loads, number of load repetitions, load profiles and frequencies of tension applied to the resistive therapy stretch cord by a user. The microprocessor control module includes further means for providing auditory and visual feedback for use in a biofeedback mode which monitors force applications applied to a body system under conditioning. The internal memory of the microprocessor control module stores biofeedback generated by the user which can be manipulated for analysis and utilization in therapy evaluation and planning, thus eliminating mere subjective evaluation of a patient's rehabilitative performance.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 4, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
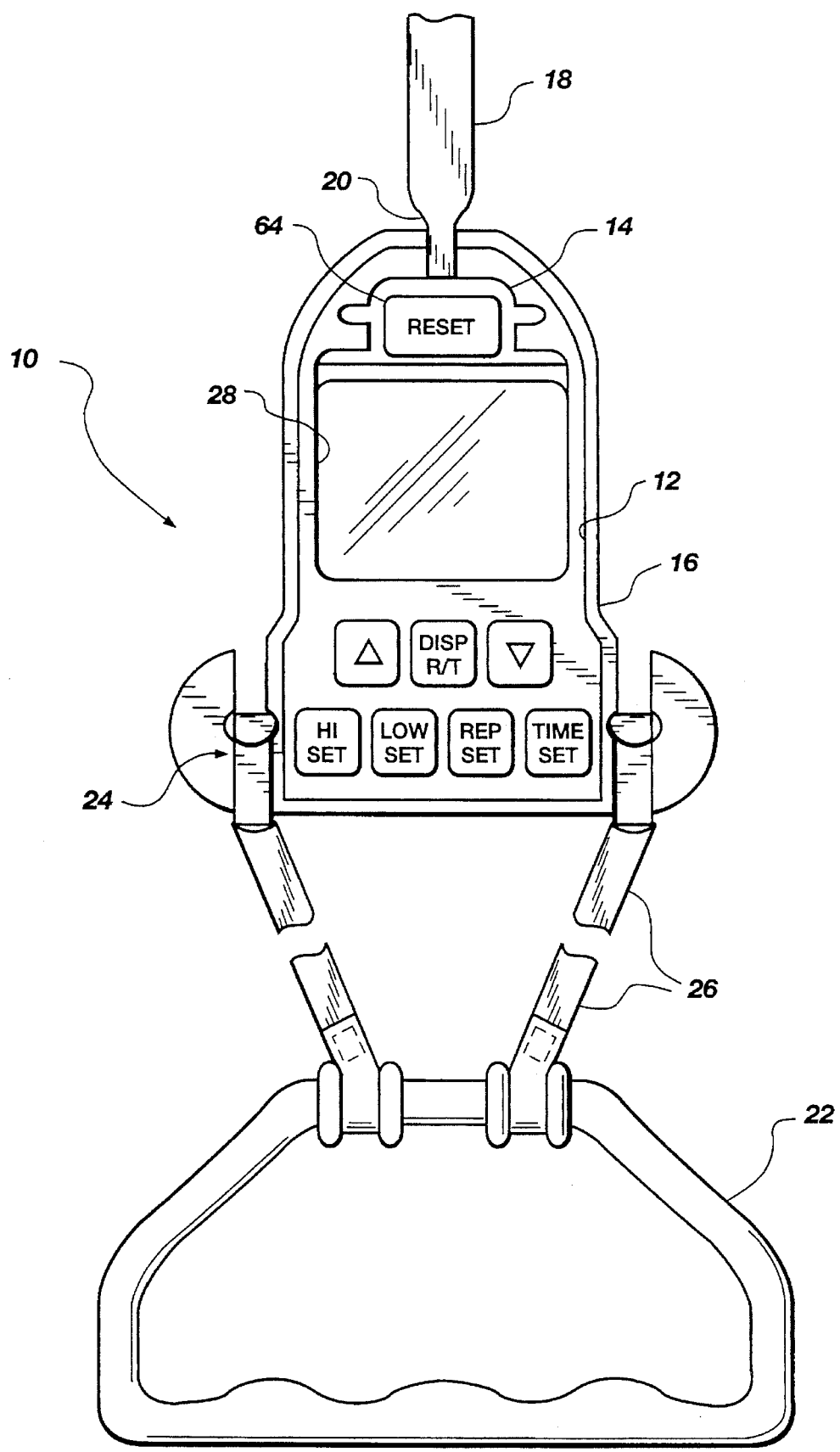
FIG. 1 is a perspective view of an instrumented therapy cord in accordance with one presently preferred embodiment of the present invention.

One presently preferred embodiment of the instrumented therapy cord of the present invention, designated generally at 10, is illustrated in FIG. 1. As shown, instrumented therapy cord 10 comprises a handle member 22, a resistive stretch cord 18 and an electronic microprocessor control module 12 operably interfacing with a load cell transducer 14. Preferably, microprocessor 12 and load cell transducer 14 are housed within a substantially rigid housing unit 16.

Intermediately positioned between handle member 22 and resistive stretch cord 18, housing unit 16 is preferably formed of a non-resilient plastic material. It will be readily appreciated, however, that other suitable substances, such as, for example, metal, wood, ceramic, fiberglass or other polymeric composite materials are possible. The exterior facing of housing unit 16 is preferably configured with external surface edges having an approximately ⅛ inch radius for purposes of providing substantially smooth, rounded external edges. A substantially smooth surface, as used herein, means that the outer edges of housing unit 16 are substantially free from roughness and/or projections. It will be readily appreciated, however, that other shapes, sizes or configurations are possible which are consistent with the spirit and scope of the present invention.

Figure 2:
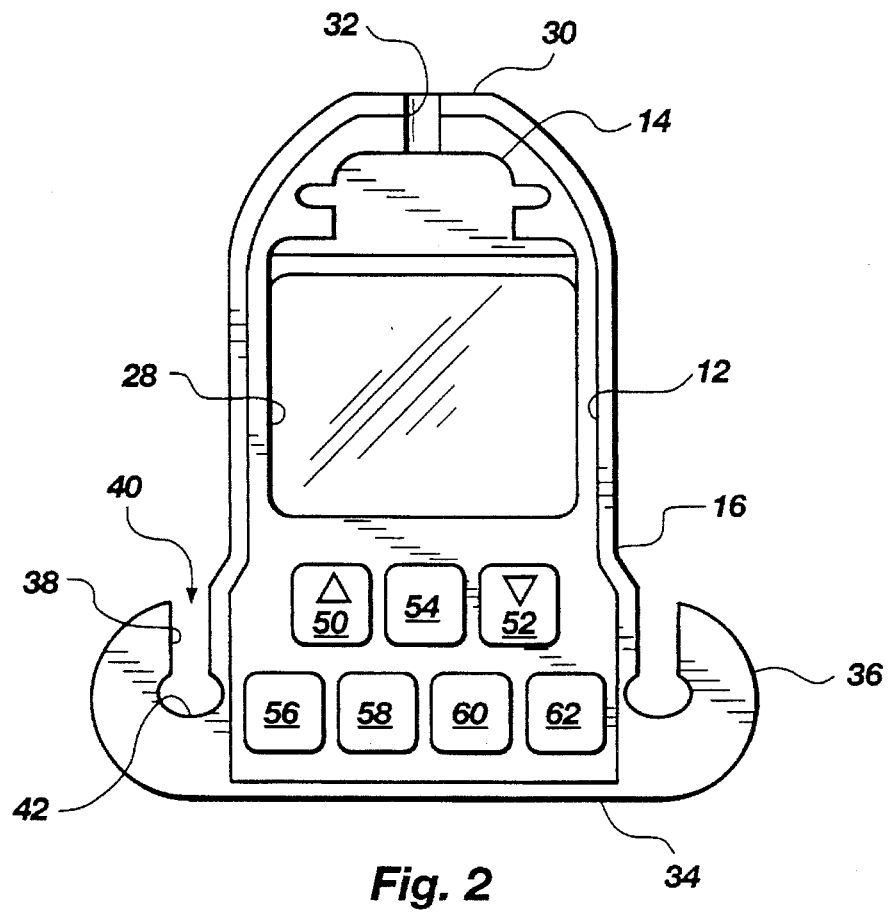
FIG. 2 is a perspective view illustrating one presently preferred embodiment of the housing unit for housing the microprocessor control module and interactive load cell transducer of one presently preferred embodiment of the present invention.

Referring now to FIGS. 1 and 2, housing unit 16 has a first end 30 having an elongated conduit 32 integrally formed therein. Elongated conduit 32 is preferably long enough in axial dimension and sufficient in cross-sectional diameter to provide means for introducing a first end 20 of resistive stretch cord 18 therethrough. In current design, resistive stretch cord 18 is preferably formed of an elastic tubing, such as, for example, standard medical tubing, a flat elastic material, such as ThetaBand™, a resilient bungee type cording, etc. First end 20 of resistive stretch cord 18 is disposed in annular alignment with elongated conduit 32 and introduced therein. In this manner, first end 20 of resistive stretch cord 18 is connected to load cell transducer 14 by means of a permanent or quick-release coupling (not shown).

A second end of resistive stretch cord 18 is preferably attached to a stationary fixation means, such as, for example, a wall anchor, a door knob, etc. by means of a permanent or releasable coupling. An alternate embodiment of the present invention provides the second end of resistive stretch cord 18 attached to a non-stationary fixation means, such as, for example, an elongated bar, a second handle member, etc. by means of a permanent or removable coupling. Pursuant thereto, those skilled in the art will readily recognize other possible modifications and adaptations which are consistent with the spirit and scope of the present invention.

Extending substantially outward and transverse the body of housing unit 16 at a second end 34 are multiple extension members 36 providing means for operably attaching handle member 22. In the preferred embodiment, housing unit 16 comprises at least two extension members 36 formed on opposing sides of housing unit 16 at second end 34. It will be readily appreciated to those skilled in the art, however, that a single extension member or a plurality of extension members can be disposed on second end 34 of housing unit 16 to provide means for attachment of handle member 22.

Figure 3:
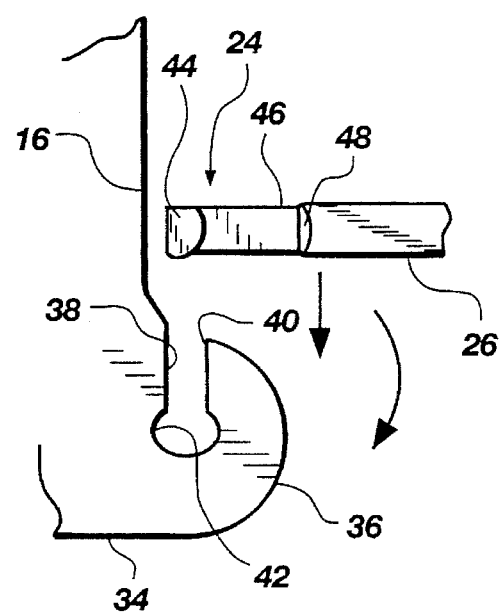
FIG. 3 is an exploded perspective view illustrating one presently preferred embodiment of an elongated channel formed in an extending member of the housing unit wherein the handle attachment member of one presently preferred embodiment of the present invention is introduced to provide an interlocking relationship between the handle and the housing unit.

Referring to the exploded view shown in FIG. 3 which illustrates one presently preferred embodiment of extension member 36 of the present invention, extension member 36 is formed having a substantially curvilinear configuration. Integrally formed within extension member 36 is an elongated channel 38. Elongated channel 38 comprises an opening 40 formed opposite a substantially spherical cross-sectional area 42. Opening 40 is preferably formed at an upper end of elongated channel 38, while cross-sectional area 42 is formed at a lower end of elongated channel 38. This general configuration of elongated channel 38 provides means for removably connecting a handle attachment member 24 securely therein, thus providing means for an interlocking engagement between handle 22 and housing unit 16 as will be discussed below.

Handle attachment means 24 preferably comprises an enlarged contoured head. 44 formed on a first end of an elongated shaft 46. Contoured head 44 is preferably formed of a substantially rigid substance, such as, for example, a resilient plastic material, and configured in such a manner so as to resemble a substantially semi-circular knuckle member. It will be readily appreciated, however, that other suitable substances, such as, for example, metal, wood, ceramic, fiberglass or other polymeric composite materials are possible. Preferably, contoured head 44 is structurally configured with a formation which is sized to substantially correspond to the width of the elongated portion of elongated channel 38 and which is substantially complimentary to the periphery of cross-sectional area 42 of elongated channel 38. Elongated shaft 46 of handle attachment means 24 is preferably formed of a resilient, semi-rigid material and comprises a linear length substantially complimentary or slightly longer than the linear length of elongated channel 38 when contoured head 44 is introduced therein.

As best shown in FIGS. 1 and 3, when introducing contoured head 44 into elongated channel 38, contoured head 44 of handle attachment means 24 is preferably positioned perpendicular to elongated channel 38 whereby aligning the cross-sectional area of contoured head 44 with the elongated cross-sectional periphery of elongated channel 38 for insertion of contoured head 44 therein. Upon insertion of contoured head 44 within elongated channel 38, contoured head 44 is substantially rotated within substantially spherical cross-sectional area 42 to a point sufficient to interlock the structural configuration of contoured head 44 within cross-sectional area 42 of extension member 36. Once contoured head 44 is interlocked within cross-sectional area 42, elongated shaft 46 of handle attachment means 24 is preferably extended across the top external facing or bottom surface of housing unit 16. Those skilled in the art will readily recognize other possible modifications and/or adaptations in order to connect handle attachment means 24 to housing unit 16 of the present invention which are reasonably consistent with and contemplated by the spirit and scope of the present invention.

Attached to a second end of elongated shaft 46 of handle attachment means 24 is a rigid securing means. As illustrated in one presently preferred embodiment of the present invention, a substantially D-shaped grommet 48 is provided as means for securing an attachment between elongated shaft 46 and a first end of connecting straps 26. Connecting straps 26 are preferably formed of a non-elastic material, such as, for example, a sufficiently sturdy cloth material. It will be readily appreciated, however, that depending on the particular bracing and holding characteristics desired, connecting straps 26 can be formed of fin elastic material.

Referring now to FIG. 1, a second end of connecting straps 26 comprises means of attachment between connecting straps 26 and handle member 22. Preferably, connecting straps 26 are passed around a linear portion of handle member 22 in a looped configuration and fastened therearound. In current design, handle member 22 is rigid and preferably formed in a substantially D-shaped configuration comprising a handle-grip formed in combination therewith. Those skilled in the art will readily recognize other possible modifications and/or adaptations of handle member 22 and the attachment arrangement between handle member 22 and connecting straps 26 of the present invention which are reasonably consistent with and contemplated by the spirit and scope of the present invention.

In practice, the second end of resistive stretch cord 18 is attached to a stationary or moveable body, while first end 20 of resistive stretch cord 18 is operably coupled to load cell transducer 14 housed within housing unit 16. Pursuant to the foregoing arrangement, a user of instrumented therapy cord 10 can apply tensile forces to resistive stretch cord 18 by pulling on handle member 22 operably engaging second end 34 of housing unit 16 by means of an interlocking connection. In this manner, the tensile forces applied to resistive stretch cord 18 can be measured by load cell transducer 14 to provide an output which is indicative of the instantaneous load force applied against resistive stretch cord 18.

Transducer 14 comprises various suitable transducer components, such as, for example, a force transducer or load cell, preamplifier circuitry and calibration arrangements. Load cell transducer 14 provides means for a mechanical coupling arrangement for first end 20 of resistive stretch cord 18 and an appropriate electronic sensor means to sense the tension generated by load forces applied to resistive stretch cord 18 through the mechanical coupling arrangement with resistive stretch cord 18.

Electronically interfacing with microprocessor control module 12, load cell transducer 14 converts mechanical energy represented by the load force applied to resistive stretch cord 18 into electronic signals which can be processed by microprocessor control module 12. Preferably, microprocessor 12 of the present invention is a self-contained unit having a battery power source to maintain cord versatility. Internal programming system routines of microprocessor control module 12 convert the electronic signals generated by load cell transducer 14 into biofeedback which represents peak and average load, number of load repetitions, load profiles, frequencies and duration of load tension maintained by the user of instrumented therapy cord 10.

Microprocessor control module 12 further comprises a plurality of biofeedback comparators connected to load cell transducer 14 which measure the load output of resistive stretch cord 18. The output of each comparator is enabled when load cell transducer 14 indicates that a corresponding one of a plurality of different preprogrammed load thresholds has been attained or exceeded, thus providing visual and audio biofeedback to the user of instrumented therapy cord 10. In addition, microprocessor control module 12 provides means for storing electronic signals generated by load cell transducer 14 within its internal memory for manipulation, recall and analysis.

In one presently preferred embodiment of the present invention, the internal systems protocol of microprocessor control module 12 provides means for interfacing with a visual display means 28, preferably a liquid crystal display (LCD), and an auditory feedback means which in combination provide visual and audio biofeedback to the user of instrumented therapy cord 10. The auditory feedback means preferably generates sound outputs using conventional internal sound controller circuitry and at least one output speaker (not shown). In current design, the auditory biofeedback means produces a beep or chirping sound when the programming parameters of instrumented therapy cord 10 are satisfied.

As shown in FIGS. 1 and 2, a plurality of input keys 50–64 are provided for initiating the internal programming system routines of microprocessor control module 12. Input keys 50–64 are preferably pressure sensitive dome keys formed on the front facing of housing unit 16. It will be readily appreciated, however, that other suitable means for initializing the internal programming of microprocessor 12, such as, for example, dial adjustments, touch sensitive switches, slide switches, momentary or non-momentary switches, etc. are possible.

Input keys 50–64 are used for initializing the operational programming parameters of microprocessor control module 12 and for displaying internal programming routines on LCD display 28 for visual review and evaluation. So as to create a range of desired force applications for resistive stretch cord 18, means for setting upper and lower force thresholds are provided by a HI SET key 56 for selecting maximum upper threshold force values and a LOW SET key 58 for selecting minimum lower threshold force values. A REP SET key 60 is also provided for selecting the number of load repetitions to be performed by the user of instrumented therapy cord 10.

To assist in the initialization of the programming system routines of microprocessor control module 12, an input key 50 is provided for entering value increases and an input key 52 is provided for entering value decreases. A TIME SET key 62 is preferably formed on the front facing of housing unit 16 to provide means for entering a specific time allowance for completion of a designed therapy routine. TIME SET key 62 acts as a convention stop watch timer by counting down to 00:00:00 at which time an audio output signal is generated by the internal sound controller circuitry of microprocessor 12 to alert the user of instrumented therapy cord 10 that the allotted time has lapsed.

After the features of the programming routines of microprocessor control module 12 are selected and entered, a DISP R/T key 54 can be actuated to review previously entered data, such as, for example, the number of load repetitions and durational time values. If a physician, physical therapist or other health care provider wishes to modify any of the selected features of the internal programming routines, a RESET key 64 is provided as means for clearing any previously entered programming selections.

The preferred embodiment of the instrumented therapy cord 10 includes a conventional serial port for downloading data generated by load cell transducer 14 and stored within the internal memory of microprocessor control module 12. The serial port provides means for interfacing with other auxiliary hardware for downloading biofeedback information collected by microprocessor control module 12 for analysis and utilization in therapy planning and patient progress evaluation.

Figure 4:
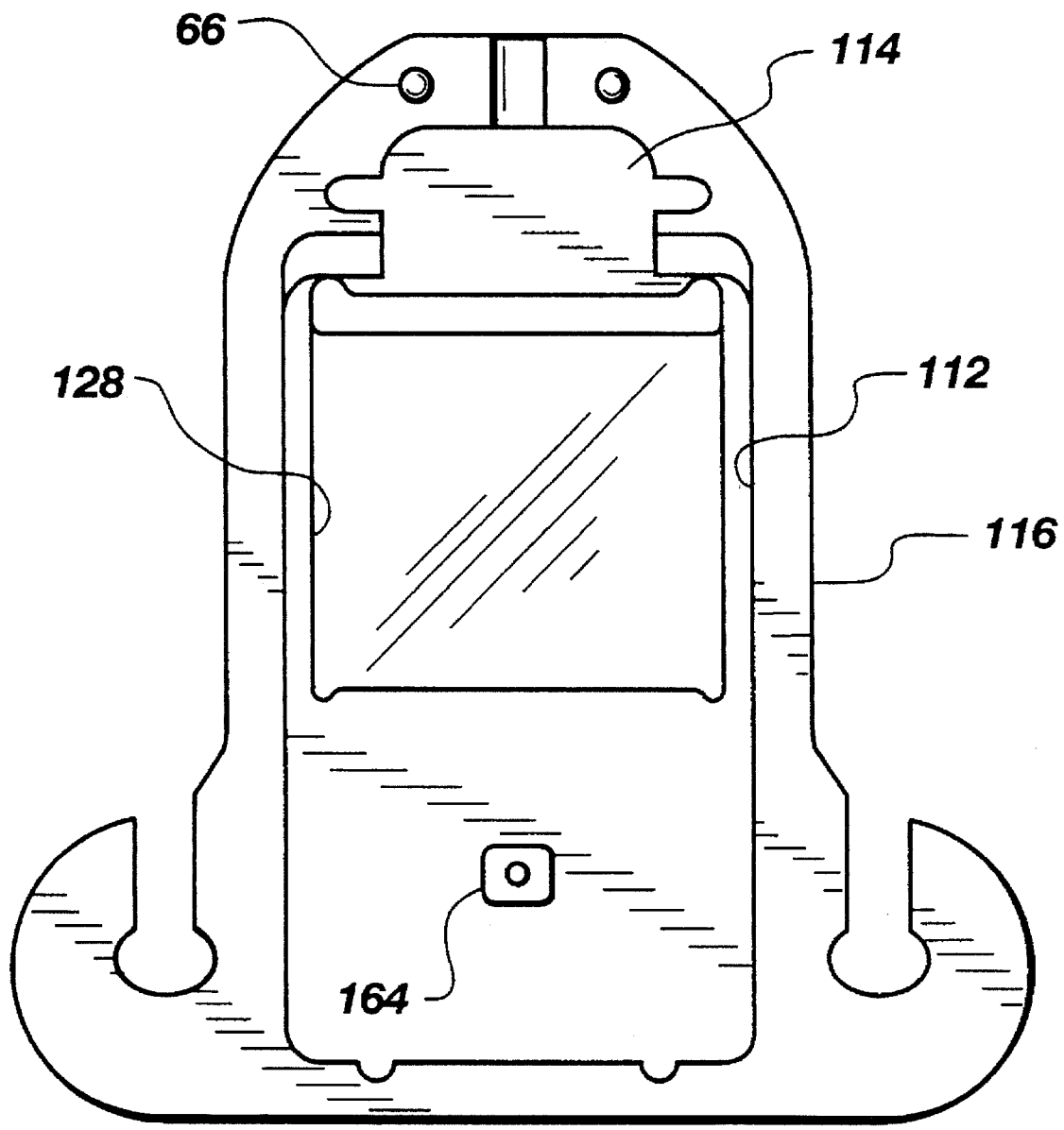
FIG. 4 is a perspective view of an alternate preferred embodiment of the present invention illustrating a housing unit for the microprocessor and interactive load cell transducer having LED lights to provide means for visual biofeedback to the operator of the instrumented therapy cord.

In addition to the foregoing, FIG. 4 illustrates an alternate preferred embodiment of instrumented therapy cord 10. This alternate embodiment is shown comprising a microprocessor control module 112 operably interfacing with a load cell transducer 114. Preferably, microprocessor control module 112 and load cell transducer 114 are housed within a substantially rigid housing unit 116 as generally described above.

The alternate preferred embodiment of the present invention has similar advantages to that of the preferred embodiment in that instrumented therapy cord 10 provides means for generating biofeedback representative of peak and average load, number of load repetitions, load profiles, frequencies and duration of load tension maintained by the user of instrumented therapy cord 10 which can be stored and recalled for objective evaluation and review. Similar to the preferred embodiment, the present alternate embodiment provides microprocessor control module 112 having an internal system routines programmed at a factory level, however, the alternate embodiment of instrumented therapy cord 10 does not require a plurality of interactive input keys for selecting the functional features of the internal programming routines of microprocessor control module 112. A RESET key 164 is provided, however, as means for resetting the internal preprogrammed routines of microprocessor control module 112.

Microprocessor control module 112 interfaces with preferably two light emitting diodes (LED) 66, a visual display means 128, preferably a liquid crystal display (LCD), and an auditory feed back means to provide biofeedback. It will be readily appreciated, however, that a single LED light 66 or a plurality of LED lights to provide visual biofeedback to the user of instrumented therapy cord 10 is consistent with the spirit and scope of the present invention.

Upon activation of instrumented therapy cord 10, the preprogrammed system routines of microprocessor control module 112 generate processing routines for encoding and storing the electronic signals generated by load cell transducer 114. Accordingly, microprocessor control module 112 comprises a plurality of biofeedback comparators connected to load cell transducer 114 which measure the load output of resistive stretch cord 18. The output of each comparator is enabled when load cell transducer 114 indicates that a corresponding one of a plurality of different preprogrammed load thresholds has been attained or exceeded, thus providing visual biofeedback by means of LED lights 66 (which flash or blink) and auditory feedback means provided by sound controller circuitry and output speakers. Those skilled in the art will readily recognize other possible modifications and/or adaptations for providing visual and audio biofeedback which are consistent with the spirit and scope of the present invention.

From the above discussion, it will be appreciated that the present invention provides an instrumented therapy cord having a microprocessor control module which is capable of providing means for displaying direct measure and description of force peaks, average loads, number of load repetitions, profiles and frequencies applied to a resistive stretch cord by a user. Unlike prior art therapy stretch cords, the present invention provides an instrumented therapy cord which is capable of providing auditory and visual biofeedback, thereby facilitating means for assessing, monitoring and controlling the patient's therapeutic treatment program.

Additionally, the present invention provides an instrumented therapy cord which incorporates a microprocessor control module having internal memory capacity for storing patient output data generated by the load cell transducer for review and/or manipulation by a physician or therapist at a later time and place. Moreover, the present invention provides an instrumented therapy cord which is capable of providing meaningful, reliable and valid measurement of therapeutic exercise for outcome evaluation or assessment, thus eliminating the need for mere subjective evaluations of a patient's rehabilitative performance.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An instrumented therapy cord comprising:
   a resistive stretch cord having a first end and a second end, said resistive stretch cord being elastically extendable between said first end and said second end, said first end being operably disposed in connection with a fixation member;
   means for applying a load force to said resistive stretch cord;
   means for generating electronic signals indicative of said load force applied to said resistive stretch cord, said means for generating said signals being operably coupled to said second end of the resistive stretch cord;
   interactive means interfacing with said generating means for processing said electronic signals;
   means associated with said interactive means for providing biofeedback; and
   a housing member being operably, connected to said means for applying said load force, wherein said housing member houses said generating means, said interactive means and said means for providing biofeedback.

2. An instrumented therapy cord as defined in claim 1 wherein said resistive stretch cord is formed of an elastic material.

3. An instrumented therapy cord as defined in claim 1 wherein said means for applying said load force to said resistive stretch cord comprises a handle assembly being releasably connected to said housing member.

4. An instrumented therapy cord as defined in claim 1 wherein said generating means comprises a load cell transducer.

5. An instrumented therapy cord as defined in claim 1 wherein said interactive means comprises a microprocessor control module having internal memory capacity for storing said electronic signals.

6. An instrumented therapy cord as defined in claim 1 wherein said means for providing biofeedback comprises a display means.

7. An instrumented therapy cord as defined in claim 6 wherein said display means comprises a liquid crystal display (LCD).

8. An instrumented therapy cord as defined in claim 6 wherein said display means comprises at least one light emitting diode (LED).

9. An instrumented therapy cord as defined in claim 1 wherein said means for providing biofeedback comprises an auditory means.

10. An instrumented therapy cord as defined in claim 9 wherein said auditory feedback means comprises sound controller circuitry and at least one audio speaker for generating sound output.

11. An instrumented therapy cord as defined in claim 1 wherein said housing member further comprises an elongated conduit where through a first end of said resistive stretch cord is introduced and operably coupled to said means for generating said electronic signals.

12. An instrumented therapy cord as defined in claim 1 wherein said housing member is formed of a non-resilient plastic material.

13. An instrumented therapy cord comprising:

a resistive stretch cord having a first end and a second end, said resistive stretch cord being elastically extendable between said first end and said second end, said first end being operably disposed in connection with a fixation member;

a handle assembly for applying a load force to said resistive stretch cord;

a transducer for generating electronic signals indicative of said load force applied to said resistive stretch cord, said transducer being operably coupled to said second end of the resistive stretch cord;

a microprocessor control module interfacing with said transducer for processing said electronic signals;

display means interfacing with said microprocessor for providing visual biofeedback;

auditory means associated with said microprocessor for providing audio feedback; and a housing member being operably connected to said handle assembly, wherein said housing member houses said transducer, said microprocessor, said display means and said auditory feedback means.

14. An instrumented therapy cord as defined in claim 13 wherein said resistive stretch cord is formed of an elastic material.

15. An instrumented therapy cord as defined in claim 13 wherein said handle assembly further comprises a releasable attachment for interlocking the handle assembly to said housing member.

16. An instrumented therapy cord as defined in claim 13 wherein said handle assembly comprises an elongated member having a contoured head formed on a first end and an attachment means formed on a second opposing end, wherein said attachment means provides an attachment for at least one connecting strap, said connecting strap being operably connected to a handle member.

17. An instrumented therapy cord as defined in claim 16 wherein said contoured head of said handle assembly is introduced into an elongated channel formed in an extension member of said housing unit, thus providing an interlocking connection therebetween.

18. An instrumented therapy cord as defined in claim 13 wherein said microprocessor control module includes internal memory capacity for storing said electronic signals.

19. An instrumented therapy cord as defined in claim 13 wherein said microprocessor control module includes external memory interface capacity for storing said electronic signals.

20. An instrumented therapy cord as defined in claim 13 wherein said housing unit comprises a plurality of input keys for selecting functional features of an internal program routine of said microprocessor.

21. An instrumented therapy cord as defined in claim 13 wherein said display means comprises a liquid crystal display (LCD).

22. An instrumented therapy cord as defined in claim 13 wherein said display means comprises at least one light emitting diode (LED).

23. An instrumented therapy cord as defined in claim 13 wherein said auditory means comprises sound controller circuitry and at least one audio speaker for generating sound output.

24. An instrumented therapy cord as defined in claim 13 wherein said housing member further comprises an elongated conduit wherethrough a first end of said resistive stretch cord is introduced and operably coupled to said transducer.

25. A method for providing therapeutic exercise using an instrumented resistive stretch cord, said method comprising the steps of:

attaching a first end of said resistive stretch cord to a fixation member;

operably coupling a second end of said resistive stretch cord to a means for generating electronic signals, said generating means being housed within a housing member wherein said generating means interfaces with an interactive means;

attaching a handle assembly to said housing member to provide an operable connection therebetween;

applying a load force to said resistive stretch cord, said resistive stretch cord being elastically extendable between said fixation member and said generating means;

generating electronic signals indicative of said load force applied to said resistive stretch cord;

processing said electronic signals; and providing biofeedback.

26. A method for providing therapeutic exercise using an instrumented therapy cord as described in claim 25 wherein said housing member houses said generating means, said interactive means and said means for providing biofeedback.

27. A method for providing therapeutic exercise using an instrumented therapy cord as described in claim 25 wherein providing biofeedback comprises a display means.

28. A method for providing therapeutic exercise using an instrumented therapy cord as described in claim 25 wherein providing biofeedback comprises an auditory means.

* * * * *

UNITED STATES PATENT AND TRADEMARK OFFICE
CERTIFICATE OF CORRECTION

PATENT NO. : 5,538,486
DATED : July 23, 1996
INVENTOR(S) : France et al.

It is certified that error appears in the above-identified patent and that said Letters Patent is hereby corrected as shown below:

In column 5, line 65, please delete "ThetaBand™", and insert therefore -- TheraBand™ --.
In column 7, line 25, please delete "fin", and insert therefore -- an --.
In column 10, line 53, after "operably" delete -- , --.
In column 11, line 23, please delete "where through", and insert therefore -- wherethrough --.

Signed and Sealed this

Twenty-fourth Day of December, 1996

Attest:

BRUCE LEHMAN

*Attesting Officer*  *Commissioner of Patents and Trademarks*